US008545729B2

(12) United States Patent
White et al.

(10) Patent No.: US 8,545,729 B2
(45) Date of Patent: Oct. 1, 2013

(54) PREPARATION OF METAL COLLOIDS

(75) Inventors: Peter Cyril White, Lincoln (GB); Jakob Howie Hjortkjaer, Copenhagen Oe (DK)

(73) Assignee: The University of Lincoln, Brayford Pool, Lincoln (GB)

( * ) Notice: Subject to any disclaimer, the term of this patent is extended or adjusted under 35 U.S.C. 154(b) by 419 days.

(21) Appl. No.: 12/808,993

(22) PCT Filed: Dec. 19, 2008

(86) PCT No.: PCT/GB2008/004225
§ 371 (c)(1),
(2), (4) Date: Jul. 20, 2010

(87) PCT Pub. No.: WO2009/081138
PCT Pub. Date: Jul. 2, 2009

(65) Prior Publication Data
US 2010/0290043 A1 Nov. 18, 2010

(30) Foreign Application Priority Data
Dec. 21, 2007 (GB) .................................. 0724870.1

(51) Int. Cl.
*B01J 13/00* (2006.01)
(52) U.S. Cl.
USPC ......... 252/500; 252/512; 252/514; 252/519.1
(58) Field of Classification Search
USPC ............................... 252/500, 512, 514, 519.1
See application file for complete search history.

(56) References Cited

U.S. PATENT DOCUMENTS 6,913,825 B2 * 7/2005 Ostafin et al. ................. 428/402
7,393,696 B2 * 7/2008 Roth et al. ..................... 436/510
2004/0241462 A1 * 12/2004 Lee et al. ....................... 428/447

FOREIGN PATENT DOCUMENTS

DE 10 2006 017 696 A1 10/2007
EP 0 426 300 A 5/1991
WO WO 97/28451 A 8/1997

OTHER PUBLICATIONS http://www.merriam-webster.com/thesaurus/predominantly General knowledge, from the world wide web on Jan. 24, 2013.*
Nitrate Wtih Hydroxylamine Hydrochloride, J. Phys. Chem B., vol. 107, No. 24, May 22, 2003, pp. 5723-5727, XP002527546, cited in the application, pp. 5724-5726.

* cited by examiner

*Primary Examiner* — Nathan M Nutter

(57) ABSTRACT

A method is described for producing a silver colloid solution comprised of highly stable resulting colloids, the method comprising: adding an aqueous solution of a hydroxylamine salt to an aqueous solution of an alkali, and then dispersing into the mixture an aqueous solution of the metal ions, the hydroxylamine salt being selected such that the anion, when combined with the said metal ions, would form a metal salt having a very low solubility in water, wherein the metal ion solution is introduced into the mixture in such a manner that the metal ions are substantially dispersed throughout the mixture within one second. A maturing period, preferably at elevated temperatures, leads to a stable state in which the characteristics of the colloid undergo no further changes, and it is preferred to make and store the colloid in a polystyrene container for greatest stability. The resulting colloids from such method exhibit high light-scattering properties of small particle size and low background fluorescence levels, with a long shelf life, making it particularly suitable for Raman spectroscopy.

22 Claims, 9 Drawing Sheets

◆ 612cm⁻¹
■ 1363cm⁻¹
▲ 1649cm⁻¹

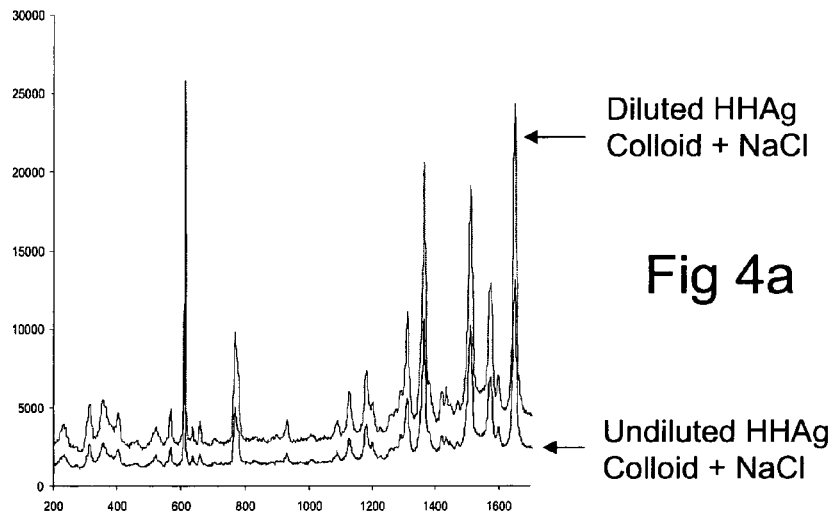
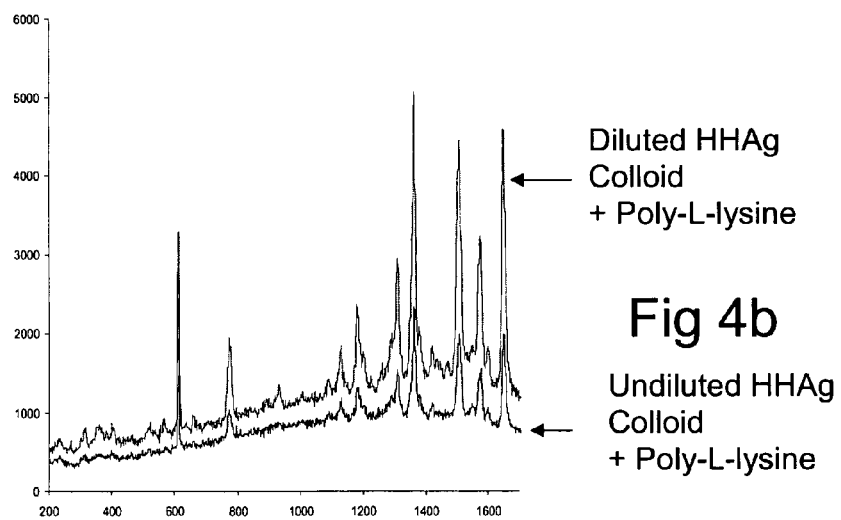
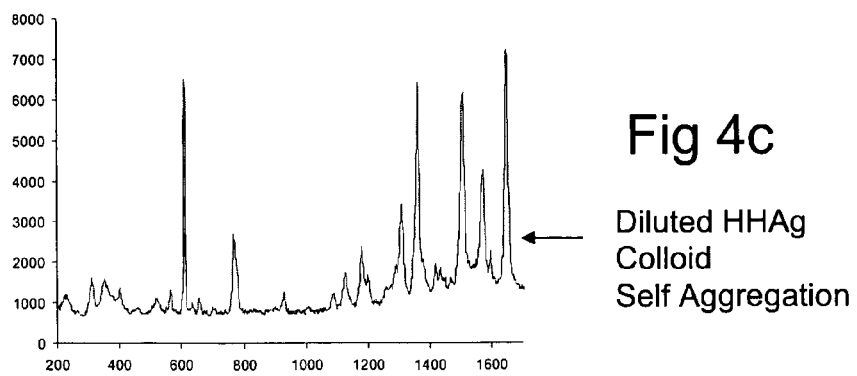

PREPARATION OF METAL COLLOIDS

FIELD OF THE INVENTION

This invention relates to a method of preparing stable metal colloids.

BACKGROUND TO THE INVENTION

For many years analytical chemists did not use Raman spectroscopy because it failed to provide the degree of sensitivity required for the detection of trace quantities of analytes. The main reason for this is the high background levels of fluorescence arising from either the sample or substrate.

In 1974, Fleischman discovered, whilst using Raman spectroscopy to study the electrochemical reactions of pyridine on a silver electrode, that there was a remarkable enhancement of the pyridine Raman signals, with the silver quenching a large amount of the background fluorescence. It is known that surface enhancement could only be achieved if the silver surface was rough and not smooth.

The possibility of utilizing colloidal dispersions of either silver (Ag) or gold (Au) in aqueous solutions was first demonstrated by Creighton and co-workers in 1979 (Creighton, J. A.; Blatchford, C. G.; Albrecht, M. G. *J Chem. Soc., Faraday Trans.* 2 1979, 75, 790). It has been found that equal or even higher surface enhancement effects can be achieved with silver colloids. A colloid is a suspension of the metal particles in solution. In order to achieve the optimum effect, controlled aggregation of the silver colloid particles is required, typically using organic or inorganic compounds as aggregation reagents.

With the tremendous increase in sensitivity that can be achieved using this surface enhancement effect, the analytical techniques of Surface Enhanced Raman Scattering (SERS) Spectroscopy and Surface Enhanced Resonance Raman Scattering (SERRS) Spectroscopy have since been developed.

The growth in the use of these techniques has been exponential but the major problem is producing stable colloids with good light scattering properties and capable of quenching background fluorescence. In order for a colloid to remain stable the silver particles should remain suspended indefinitely, but it is known that on many occasions aggregation occurs and the silver falls out of solution.

Silver colloids can be prepared by chemical reduction with either sodium borohydride or sodium citrate. It is well known that citrate reduced colloids are more stable and many analysts have prepared these using a method published by P. C. Lee and O. Meisel (*J. Phys. Chem.,* 1982, 86, 3391-3395). However, it is well known that batch-to-batch reproducibility is difficult to achieve by this method and the stability, i.e. shelf life, is variable. Preparation of such silver colloids using this method requires the use of ultra clean glassware and accurately controlled temperatures, stirring speed, etc.

Since this original published method there has been a published modification of this original method (C. H. Munro, W. E. Smith and P. C. White, *Analyst* 1993, Vol. 118. 733-735). This published modification of the original known method led to some improvements in the properties of the silver colloid but long term stability of the colloids still remained a problem.

Prior attempts at producing silver colloids with desirable light scattering properties have been poor and because of these disappointing results there has been little encouragement to go against the perceived wisdom that the ionic nature of sodium in silver nitrate was in fact responsible for the failed attempts at obtaining silver colloids with suitable stability and shelf-life. In WO2007/107792 we disclose and claim a method of producing very stable silver colloids with good SERRS properties using lithium citrate instead of sodium citrate to reduce silver nitrate.

The use of hydroxylamine hydrochloride to reduce silver nitrate at alkaline pH and at room temperature was published in Leopold, N.; Lendi B,; *J. Phys, Chem. B* 2003, 107, 5723-5727. The results published in this paper show that the colloids have a high bandwidth and $\lambda_{max}$ values with a large particle size distribution. These properties are typical of poor colloids and would not be expected to give good SERRS spectra. The spectra presented show high levels of fluorescence background, which is typical of poor adsorption of the dye on to the silver particles. There is no mention in the paper of the stability or reproducibility of SERRS spectra from different batches of colloid, and this has been the major problem in SERRS spectroscopy.

Gold colloids can be used in various nanotechnology applications, for example in biosensors, as well as in Raman Spectroscopy. Other metals in colloidal form may be applicable to similar applications, or may find new applications.

SUMMARY OF THE INVENTION

In accordance with the present invention, a method of producing a metal colloid solution comprises adding an aqueous solution of a hydroxylamine salt to an aqueous solution of an alkali, and then dispersing into the mixture an aqueous solution of the metal ions, the hydroxylamine salt being selected such that the anion, when combined with the said metal ions, would form a metal salt having a very low solubility in water, wherein the metal ion solution is introduced into the mixture in such a manner that the metal ions are substantially dispersed throughout the mixture within one second, and preferably within 0.5 second.

The introduction of the metal ions might be achieved by rapid injection via a high velocity jet. Currently, this is achievable best by using very small volumes of the solutions, for example injecting a small volume of the metal ion solution into the hydroxylamine solution using a plunger pipette. The method of the invention may advantageously employ high-speed, low volume injection techniques such as those used in ink-jet printers, where small droplets are ejected rapidly and at high velocity.

The metal ion is suitably silver or gold, although other ions, such as copper, may also be used to produce colloids. The silver may be in the form of silver nitrate solution.

The alkali is preferably a strong base such as sodium hydroxide or potassium hydroxide, sodium hydroxide being preferred. The alkali solution is preferably freshly prepared, as it is believed that absorption of carbon dioxide from the atmosphere affects the result—it has been found that the use of sodium hydroxide which has been standing for some time, even for a period of two hours, resulted in a darker colloid with higher $\lambda_{max}$, decreased absorbance and larger bandwidth values.

Results have shown that the optimum period for producing colloids with the most desirable UV and SERRS properties is where the subsequent mixing step is conducted so as to achieve full dispersion within 10 seconds. When the mixing step is conducted in a shorter period (2 seconds) or a longer period (30 seconds), this produces significantly poorer results in the form of unstable colloids.

The colloids produced by the applicant's method are shown to exhibit outstanding UV properties. For a diluted colloidal preparation (60 µl of colloid in 3 ml of water) in a 1 cm path length cuvette, this produces a UV spectrum which exhibits a $\lambda_{max}$ value of typically 389±1 nm, a bandwidth of 28±2 nm and an absorbance of 0.475±25. The resulting colloids also gave very intense SERRS spectra and lower fluorescence background than the applicant's previous results obtained when using lithium citrate as the reducing agent.

The reduction of metal salts produces metal particles, and anions present in the solution are attracted to the surface of the particle. Provided the charge remains on the particles they will be repelled from each other and remain in solution. Ideally, the metal particles in a colloidal solution should remain in solution indefinitely, but in the production of many colloids this stability is not achieved and aggregation of the particles occurs with time, resulting in collapse of the colloid. Proof of this occurring can be monitored by UV, where an increase in $\lambda_{max}$, and bandwidth, and lowering of absorbance, are observed over a period of time.

In the applicant's proposed method for the production of colloids, the choice of the hydroxylamine salt, i.e. the anion, was found to influence the stability of the colloid. In the preparation of silver colloids with different salts of hydroxylamine, no stable colloid could be obtained with the sulphate, nitrate or O-sulphonic acid salts. With the hydrochloride salt, colloids with limited stability can be obtained but with the phosphate salt a very stable colloid can be produced. The increased instability observed can be related to the insolubility, i.e. stability constant ($K_{sp}$) of the silver salt—$K_{sp}$ $Ag_2SO_4=1.2\times10^{-5}$; $AgCl=1.8\times10^{-10}$ and $Ag_3PO_4=1.2\times10^{-16}$.

It is also believed that the valency of the anion affects the stability of the colloid. With Lee and Meisel citrate reduced colloids, the silver citrate has a $K_{sp}$ very similar to that of silver sulphate and hence would not be expected to be very stable. However, citrate is a trivalent anion and this possibly accounts for the higher degree of stability than expected. Hence with phosphate also being a trivalent anion this could also account for the improved stability achieved with hydroxylamine phosphate. Using the applicants' proposed method of preparation a gold colloid has been produced, but a stable form could only be achieved with phosphate and not the hydrochloride salt of hydroxylamine. Hence the method uses a hydroxylamine salt selected such that the anion is of high valency, and when combined with the said metal ion would form a metal salt having a low solubility in water. Silver nitrate, gold chloride or copper nitrate may, for example, be used as the metal ion solution.

Silver colloids produced using hydroxylamine hydrochloride (HHAg colloids) show within 48 hours of production a reduction of bandwidth and $\lambda_{max}$ with increased absorbance in their UV properties. After this period of time $\lambda_{max}$ and the bandwidth reduce at a much slower rate, with no major change in absorbance over 30 days, but beyond this period the absorbance is observed to fall quite quickly. Colloids produced by using hydroxylamine phosphate (HPAg colloids) show much greater stability. Over a period of 30 days these show no major initial changes in their UV properties and over the long-term period show only very small decreases in their bandwidth and $\lambda_{max}$ values and retain their level of absorbance.

It has further been found that maturing the colloid for a predetermined period will produce a stable colloid whose properties undergo no further changes. The period of maturing is influenced by temperature. At room temperature, the maturing period may extend to about 8 weeks, but at higher temperatures the time taken to achieve stability is substantially decreased, taking, for example, only around 24 hours at 40-50° C. The maturing process is also facilitated by the size of the container, and it is preferred to use a container having a large surface area for a given volume. The use of other plastics containers, such as those made from polycarbonate, polypropylene and polyethylene terephthalate (PET), results in earlier collapse of the colloid, as do glass containers. Stability is also influenced by the material of the container in which the colloid is stored, and it has been found that polystyrene containers give the greatest stability.

The silver colloid produced by the method of the invention contains a silver concentration of 0.114 mg ml$^{-1}$, which is very similar to the silver concentration in a citrate-reduced Lee and Meisel colloid. However, unlike the latter, the HHAg and HPAg colloids produce a considerable increase in sensitivity of SERRS signals when a diluted solution of the colloid is used. The dilution is preferably within the range of 25 to 70%, and this can be achieved by using, for example, water and/or aqueous solutions of inorganic aggregating agents such as sodium chloride, nitric acid, or organic aggregating agents such as poly-L-lysine.

For SERRS, aggregation of the silver particles is essential to achieve the surface enhancement effect. Typically, with Lee and Meisel citrate-reduced colloids, if analyte concentrations greater than $10^{-5}$ M are analysed, then the phenomenon of self-aggregation occurs. In order to detect analytes at lower concentrations, inorganic or organic aggregating agents have to be used. Studies performed with the HHAg colloids show over the first 48 hours life of the colloid that it is possible to achieve self-aggregation at lower concentrations (around $10^{-8}$ M) and obtain strong SERRS signals, thus overcoming any need for an aggregating agent and any further dilution of the sample. Self-aggregation studies with iron-bound proteins, i.e. Cytochrome C (Cyt C), Haemoglobin (Hb) and Myoglobin (Mb) at a concentration of $10^{-7}$ M have been achieved.

With HHAg colloids older than 48 hours intense SERRS spectra can only be achieved by the addition of an aggregating agent. The unique properties of this colloid are attributed to the presence of chloride ions (from the hydroxylamine hydrochloride) being present. Chloride ions have traditionally been used as an aggregating reagent and this would explain why self aggregation can be achieved. The need to add an aggregating agent after about 48 hours indicates a growth of the aggregates to a size where they are precipitated from the solution and reducing the chloride concentration below the level required for self aggregation. The loss in UV absorbance and some visible darkening of the colloidal solution after being allowed to stand would indicate the latter occurring When compared with a previous SERRS study of Mb, in which a sodium citrate-reduced colloid with an aggregating agent was used (Abdali, S., Johannessen, C., Nygaard, J. and Norbygaard, T., *J. Phys. Condens. Matter*, 2007, 19, 285205-285212), the HHAg colloid, prepared according to the original Lendl method, produced substantially lower background fluorescence. Furthermore, the variations observed between the spectra indicate differences in the surface chemistries of the hydroxylamine- and sodium citrate-reduced colloids.

Studies with the HPAg colloids show that they are more similar to the Lee and Meisel citrate reduced salts since they do not show any level of self aggregation for analyte concentrations above $10^{-7}$ M. However, on addition of an aggregating agent very strong SERRS spectra can be obtained with very low levels of background fluorescence.

It has been observed that the HPAg colloids have a unique property. Benzotriazole dyes have been used previously as analytes to ascertain from UV studies the self aggregation properties of colloids and estimate the dye concentration at which monolayer coverage of colloidal particles occur (Faulds, K., Littleford, R. E., Graham, D., Dent, G. and Smith, W. E., *Anal. Chem.,* 2004, 76, 592-598). A similar study with the HPAg colloids have also shown that self-aggregation occurs in the range of $1\times10^{-6}$ to $1\times10^{-7}$ M but in comparison with a Lee & Meisel citrate reduced colloid, the UV shows a strong narrower bandwidth absorbance at a shorter wavelength, e.g. approximately 650 nm. compared with about 720 nm. These results indicate that due to the smaller particle size of the HPAg colloids, smaller aggregated clusters are produced and therefore have a lower plasmon wavelength than a Lee and Meisel citrate reduced silver colloid. The observed effect is also very concentration-dependent and the maximum effect occurs within the concentration range of $5\times10^{-7}$ to $7.5\times10^{-7}$ M. TEM of these solutions show discrete clumps (70×115 μm) of aggregated particles and when using a 633 nm laser, the intensity of the Raman spectra maximise in the concentration range $5\times10^{-7}$ to $7.5\times10^{-7}$ M. Hence it is possible to get a more accurate estimation of the concentration of the dye at which monolayer coverage of the colloidal particles occur. Furthermore, although only over a limited concentration the HPAg colloid provides a unique surface enhanced method for analysis of a yellow dye with a red (633 nm) laser wavelength.

These results indicate that with this method of preparation it is possible to achieve much lower levels of detection than has previously been obtained by others skilled in the art of SERRS Spectroscopy.

BRIEF DESCRIPTION OF THE DRAWINGS

In the drawings, which illustrate graphically the results of studies into colloids produced by methods according to the invention:

FIG. 4a is a plot of Raman intensity against wave number (cm$^{-1}$) illustrating the increase in SERRS sensitivity of Rhodamine 6G ($10^{-8}$ M) when using a 50% dilution of the hydroxylamine hydrochloride-reduced colloid with sodium chloride as the aggregating agent (514 nm);

FIG. 4b is a similar plot illustrating the increase in SERRS sensitivity of Rhodamine 6G ($10^{-8}$ M) when using a 50% dilution of the hydroxylamine hydrochloride-reduced colloid with poly-L-lysine as the aggregating agent (514 nm);

FIG. 4c is a plot illustrating the SERRS sensitivity of Rhodamine 6G ($10^{-8}$ M) when using a 50% dilution of the hydroxylamine hydrochloride-reduced colloid with no aggregating agent (514 nm);

DETAILED DESCRIPTION OF THE ILLUSTRATED EMBODIMENT

An exemplary method in accordance with the invention comprises adding an aqueous solution of hydroxylamine phosphate (volume 100 μl; concentration $0.075\times10^{-3}$ M with respect to hydroxylamine) to an aqueous solution of sodium hydroxide (volume 4.5 ml; concentration $1.33\times10^{-3}$ M) in a polystyrene vial, and allowing the resultant mixture to stand for a predetermined period, (ideally for a period of 30 seconds), introducing into the mixture an aqueous $10^{-2}$ M solution of silver nitrate (volume 500 μl), and mixing the solutions together, the silver nitrate solution being introduced into the mixture rapidly (less than 0.5 seconds) and the mixing is conducted so as to disperse the silver nitrate fully in the mixture within a period between 2 seconds and 30 seconds. The capped and sealed container is then heated at 40-50° C. for 24 hours, whereby a stable colloid is produced.

Figure 1:
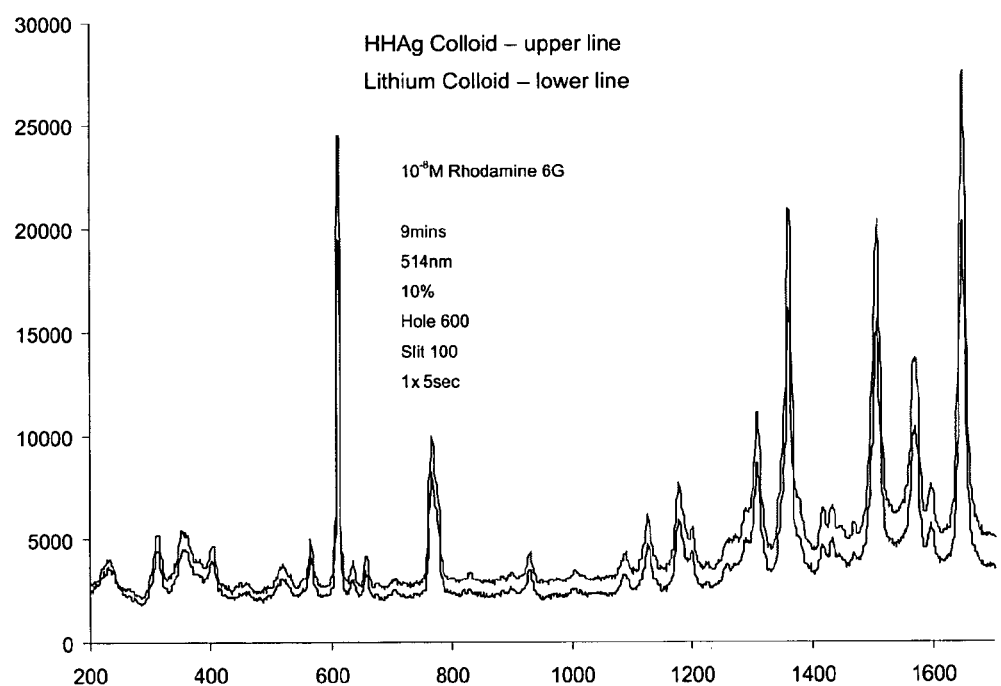
FIG. 1 is a graph of Raman intensity against wave number comparing the results obtained from the hydroxylamine hydrochloride colloid with the results obtained in the applicants' previous studies using lithium citrate.

For the preparation of the gold chloride the same method is used except that hydrogen tetrachloroaurate is used in place of the silver nitrate FIG. 1 compares previous results obtained using lithium citrate to reduce the silver nitrate, with more recent results using hydroxylamine hydrochloride to reduce silver nitrate. The sample is a $10^{-7}$ M solution of Rhodamine 6G aggregated with 0.175 NaCl solution which gives a final concentration of $10^{-8}$ M of the dye. The laser wavelength used was 514 nm.

Figure 2A:
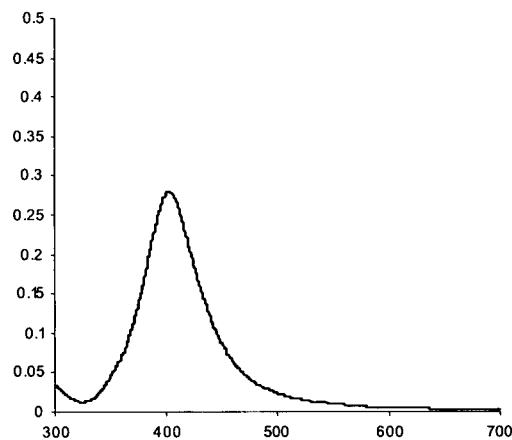
FIG. 2a is a UV/Visible spectum of a silver colloid obtained using hydroxylamine hydrochloride as the reducing agent and following the method published in Leopold, N.; Lendi B,; *J. Phys, Chem. B* 2003, 107, 5723-5727)
Figure 2B:
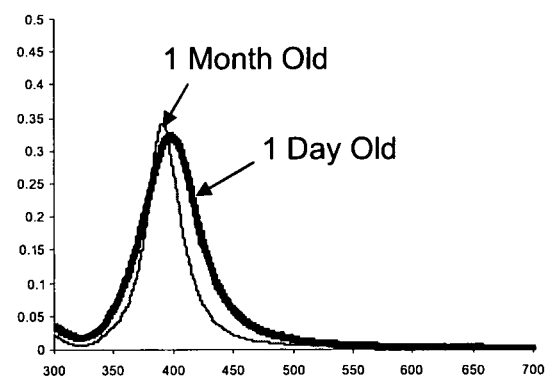
FIG. 2b shows UV/Visible spectra of a silver colloid obtained in accordance with the method of the invention using hydroxylamine hydrochloride as the reducing agent, showing the stability of the colloid over 30 days.
Figure 2C:
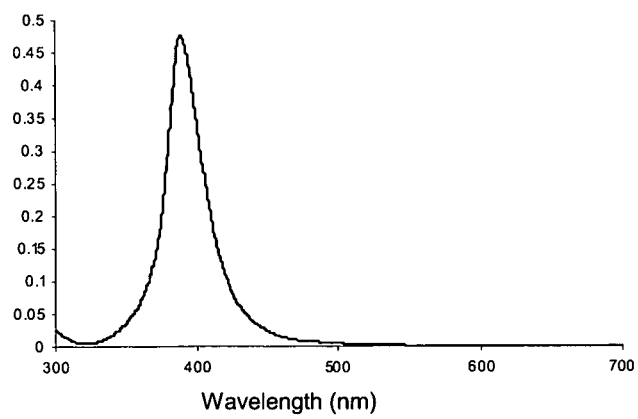
FIG. 2c shows UV spectra of a silver colloid obtained in accordance with the method of the invention using hydroxylamine phosphate as the reducing agent, showing the stability of the colloid over 7 months.

FIG. 2 compares the UV results obtained from mixing 60 μl of colloid with 3 ml of water and subsequent analysis in a 1 cm path length cuvette. FIG. 2a shows production of colloid using hydroxylamine hydrochloride as the reducing agent according to the method of Leopold, N.; Lendl, B.; *J. Phys, Chem. B* 2003, 107, 5723-5727. FIG. 2b shows the method according to the invention of reducing silver nitrate with hydroxylamine hydrochloride and the stability of the colloid over a period of one month. FIG. 2c shows the method according to the invention of reducing silver nitrate with hydroxylamine phosphate and the stability of the colloid over a period of seven months.

These results therefore demonstrate that the outstanding results achieved by the applicant are related to choice of hydroxylamine salt, the specific ratio of volumes used, the speed and duration of mixing, and the small particle size of the resulting colloids giving them increased stability and light scattering properties.

Figure 3A:
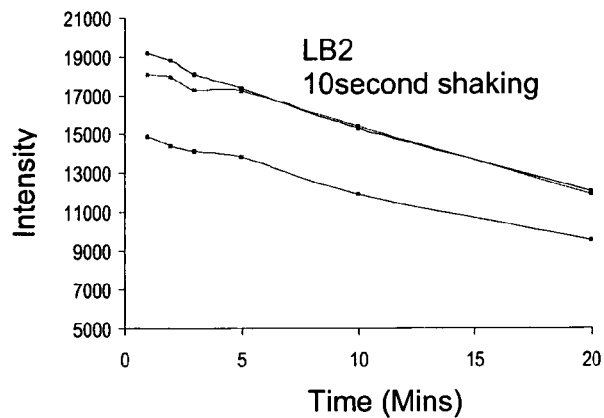
FIG. 3a is a graph of SERRS intensities (1649, 1363 and 612 cm$^{-1}$ signals for Rhodamine 6G) against time, illustrating the results obtained wherein the introduction and mixing steps are conducted so as to achieve full dispersion of HHAg colloids within 10 seconds.

FIG. 3a illustrates that when the mixing step between the aqueous hydroxylamine hydrochloride and aqueous sodium hydroxide with the aqueous solution of silver nitrate is conducted so as to achieve full dispersion within 10 seconds, the resulting colloids are both stable and possess desirable UV and SERRS properties.

Figure 3B:
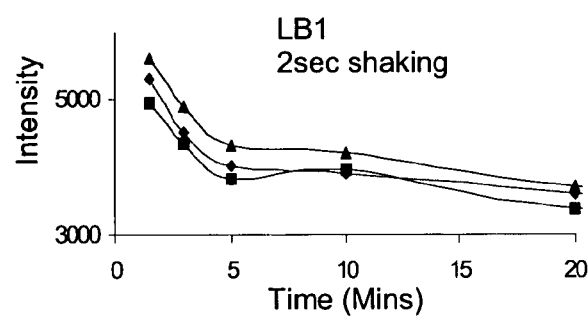
FIG. 3b is a similar graph illustrating the results obtained wherein the introduction and mixing step for producing HHAg colloids is conducted within a shorter period of 2 seconds.

FIG. 3b shows the results of replicated studies, where the mixing step is conducted within a shorter period of time of 2 seconds. It is evident from the results that the resulting colloids are unstable. This is demonstrated by the fact that with time the colloids show signs of destabilisation, indicated by the decrease in Raman intensity rapidly over a short period.

Figure 3C:
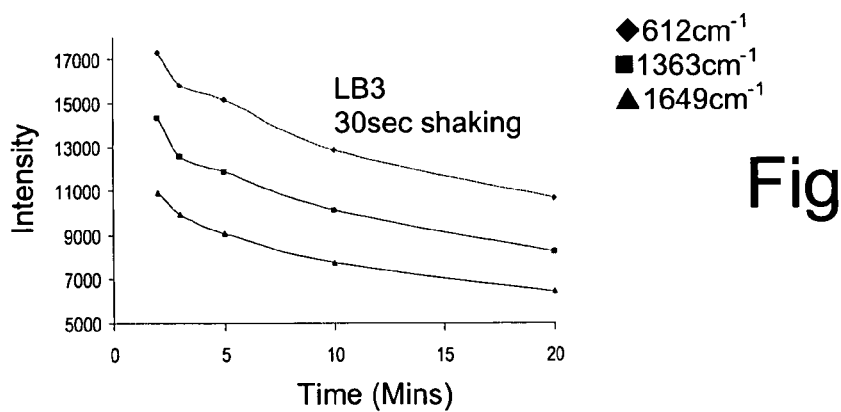
FIG. 3c is a further similar graph illustrating the results that show destabilisation of the colloids wherein the introduction and mixing step for producing HHAg colloids is conducted within a longer period of 30 seconds.

FIG. 3c shows the results obtained where the mixing step is conducted over a longer period of 30 seconds, this figure indicates the instability of the resulting colloids and demonstrates aggregation and destabilisation of the colloids.

FIGS. 3b and c demonstrate the significantly poorer results and unstable colloids that are obtained when the mixing period is altered above and below the optimum period in which full dispersion is achieved of 10 seconds.

FIG. 4a illustrates the results showing the increase in SERRS sensitivity of Rhodamine 6G ($10^{-8}$ M) when using a 50% dilution of the HHAg-reduced colloid with sodium chloride as the aggregating agent. (514 nm).

FIG. 4b illustrates the results showing the increase in SERRS sensitivity of Rhodamine 6G ($10^{-8}$ M) when using a 50% dilution of the HHAg-reduced colloid with poly-L-lysine as the aggregating agent (514 nm).

FIG. 4c illustrates the SERRS sensitivity of Rhodamine 6G ($10^{-8}$ M) when using a 50% dilution of the HHAg colloid with no aggregating agent (self-aggregation) (514 nm).

Figure 5:
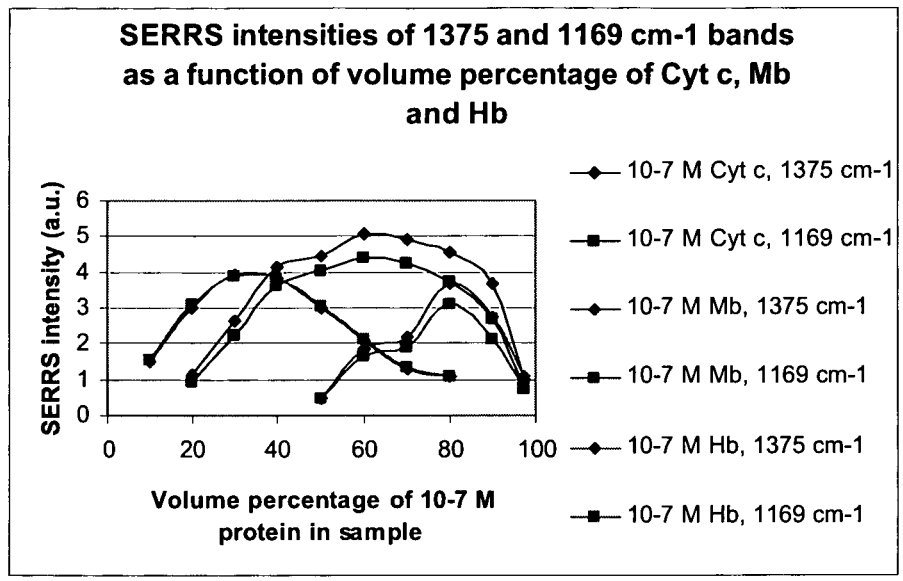
FIG. 5 is a graph of SERRS intensity (a.u.=arbitrary units) against volume percentage of $10^{-7}$ M protein in the sample, illustrating self-aggregation and the SERRS intensities achieved for the 1375 and 1169 cm$^{-1}$ bands of iron-bound proteins, CytC Mb and Hb; the plots show optimised SERRS conditions (HHAg colloid:analyte volume ratio) for each protein at a concentration of $10^{-7}$ M

FIG. 5 illustrates self-aggregation and the SERRS intensities achieved for the 1375 and 1169 $cm^{-1}$ bands of the iron-bound proteins, CytC, Mb and Hg. Plots show optimised SERRS conditions (HHAg colloid:analyte volume ratio) for each protein at a concentration of $10^{-7}$ M.

Figure 6:
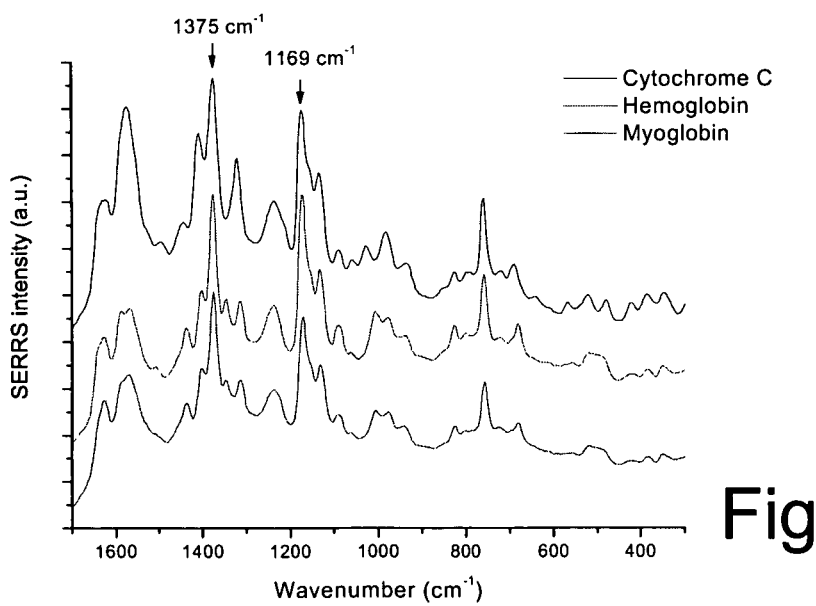
FIG. 6 is a graph of SERRS intensity against wave number illustrating self-aggregation SERRS spectra of the iron-bound proteins CytC, Mb and Hb (each protein at a concentration of $10^{-7}$ M) under the optimised SERRS conditions.

FIG. 6 illustrates self-aggregation SERRS spectra of the iron-bound proteins, CytC, Mb and Hg (each protein at a concentration of $10^{-7}$ M) under the optimised SERRS conditions with a HHAg reduced colloid.

Figure 7:
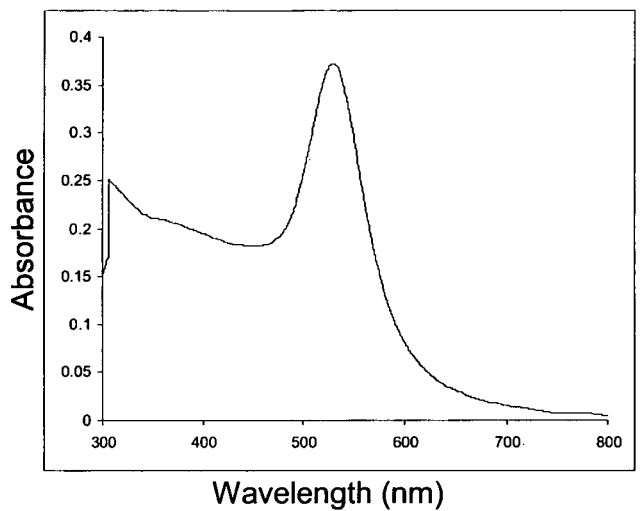
FIG. 7 is a UV/Visible spectrum of a gold colloid produced in accordance with the method of the invention using hydroxylamine phosphate as the reducing agent.

FIG. 7 illustrates the UV spectrum of a gold colloid produced the applicant's method of reducing hydrogen tetrachloroaurate with hydroxylamine phosphate. The colloid was diluted by a factor of five with water and analysed in a 1 cm path length cuvette.

Figure 8:
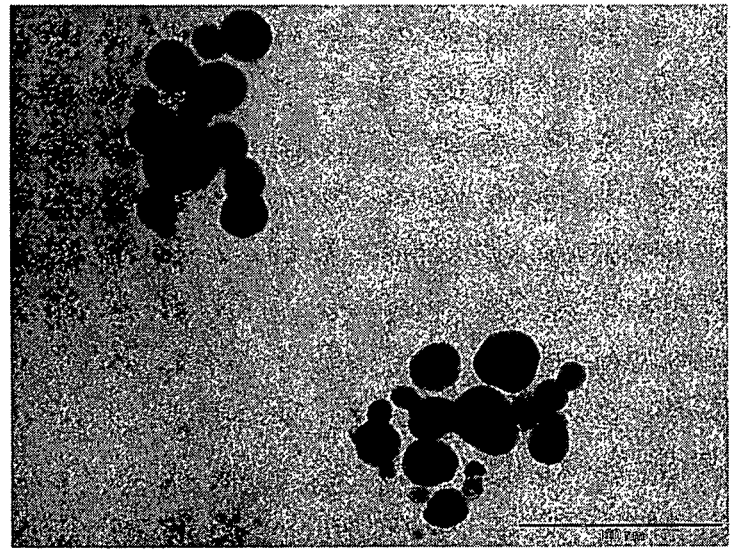
FIG. 8 is a TEM (Transmission Electron Microscope) image of an HPAg colloid aggregated with a $7.5\times10^{-7}$ M solution of a benzotriazole dye.

FIG. 8 illustrates a TEM image showing the aggregation of an HPAg colloid with a $7.5 \times 10^{-6}$ M solution of 3,5-dimethoxy 4-(5'axobenzotriaxoyl) phenylamine. Magnification=×220,000.

Figure 9:
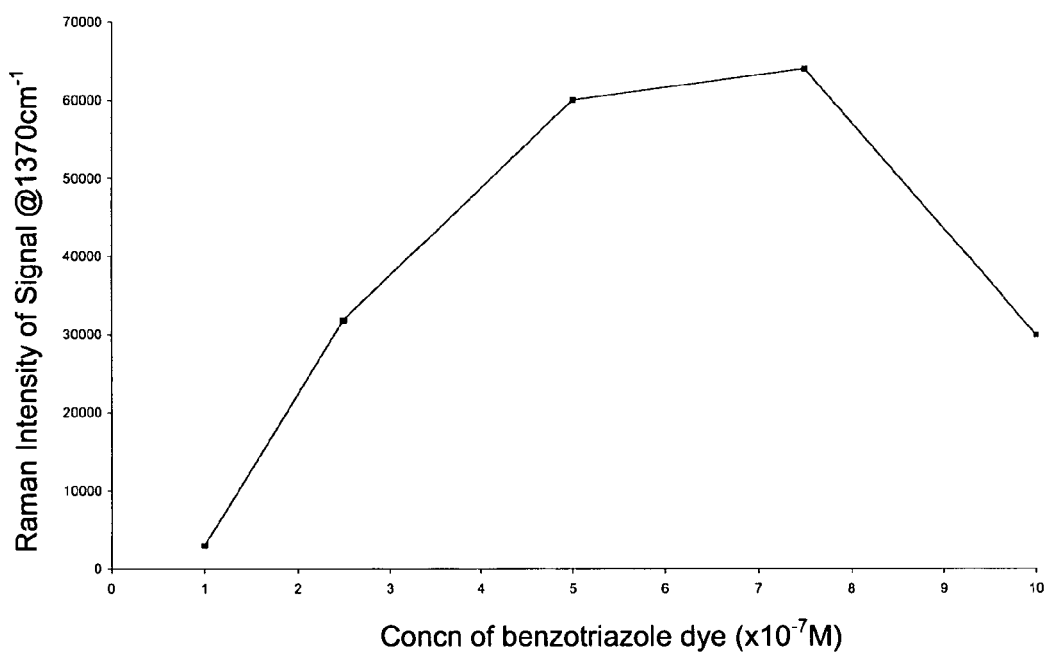
FIG. 9 is a graph of concentration versus Raman intensity of the 1368 cm$^{-1}$ signal for a benzotriazole dye using a laser wavelength of 633 nm.

FIG. 9 illustrates the effect of concentration of 3,5-dimethoxy 4-(5'axobenzotriaxoyl) phenylamine on the aggregation of an HPAg colloid (one tenth dilution) by monitoring the Raman intensity of the 1370 $cm^{-1}$ signal. Laser wavelength=633 nm with a 1×10 sec accumulation and 10% filter.

Figure 10A:
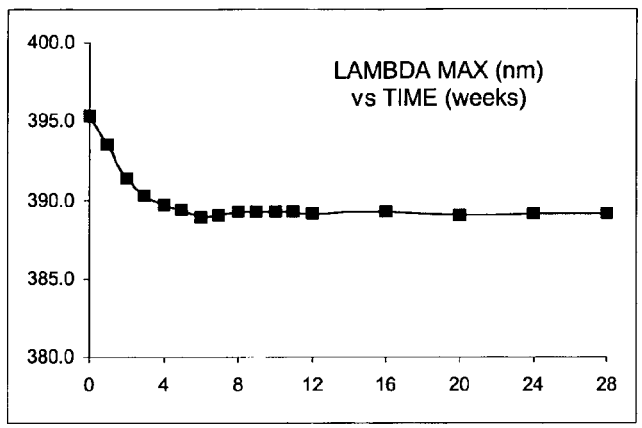
FIG. 10 shows the effect of maturing at room temperature on the UV spectral properties of a silver colloid obtained in accordance with the method of the invention, using hydroxylamine phosphate as the reducing agent, with FIG. 10a plotting $\lambda_{max}$ against time (weeks), FIG. 10b plotting Bandwidth against time, and FIG. 10c plotting Absorbance against time.
Figure 10B:
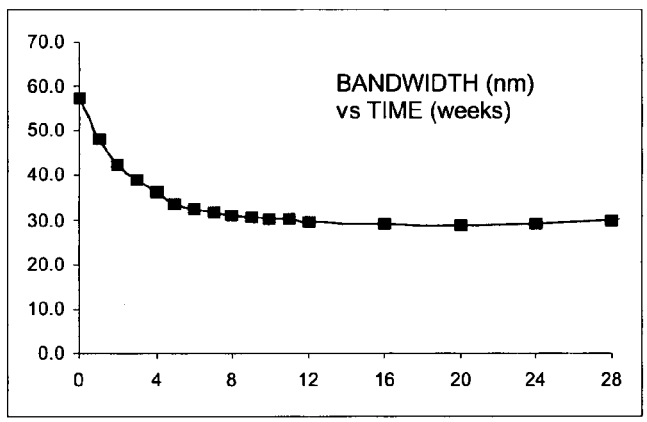
Figure 10C:
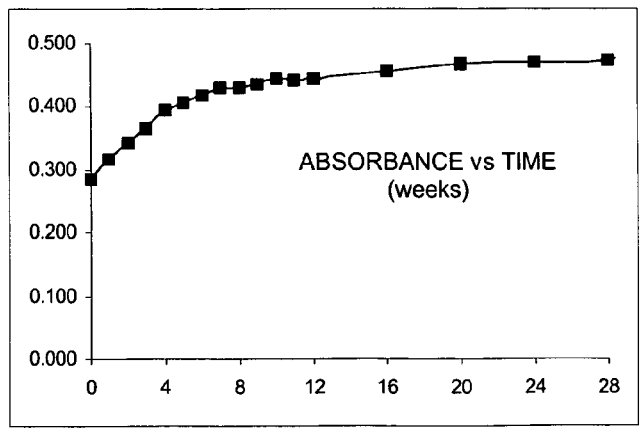

FIG. 10 shows the change in UV spectral properties during the room temperature maturing period of a colloid produced according to the method of invention of reducing silver nitrate with hydroxylamine phosphate.

Figure 11:
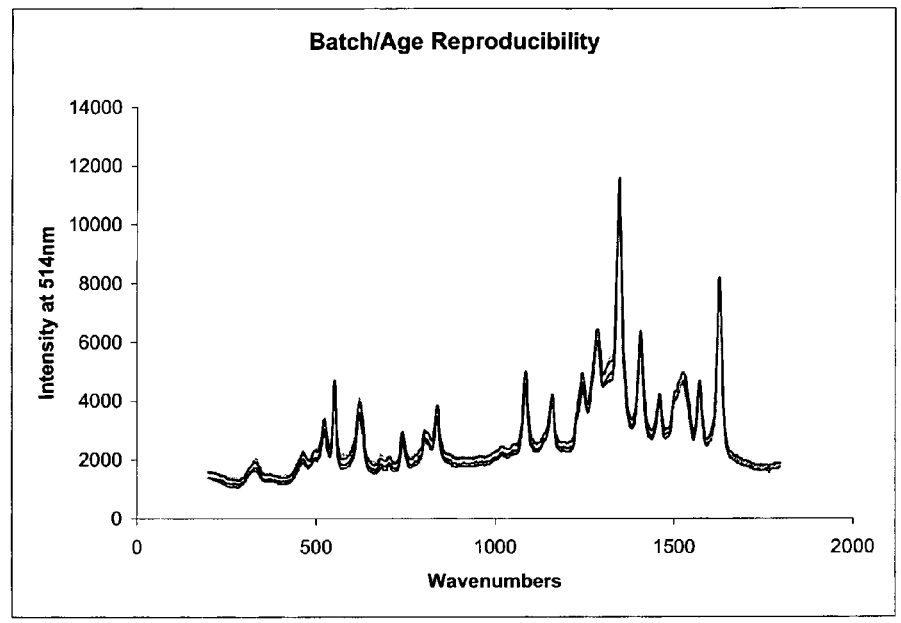
FIG. 11 illustrates the SERS spectra of Riboflavin obtained from four different aged batches of silver colloid obtained by maturing at room temperature and in accordance with the method of the invention using hydroxylamine phosphate as the reducing agent.

FIG. 11 illustrates the SERS spectra obtained with Riboflavin at concentration of $10^{-6}$ M using batches of colloid that were 6, 9, 16, and 24 weeks old produced according to the method of invention of reducing silver nitrate with hydroxylamine phosphate and matured at room temperature. These results show that although the colloid is still maturing up to about eight weeks the SERS intensity of Riboflavin only increases by less than 5% with no further increase with the older batches. These results confirm long shelf life, excellent batch to batch and SERS reproducibility of the colloid. Riboflavin is also a highly fluorescent compound and the low fluorescence level observed can be attributed to the high fluorescence quenching property of the HPAg colloid. Poly (L-Lysine) at a concentration of (0.01% w/v) was used as the aggregating agent. The laser wavelength was 514 nm.

Figure 12:
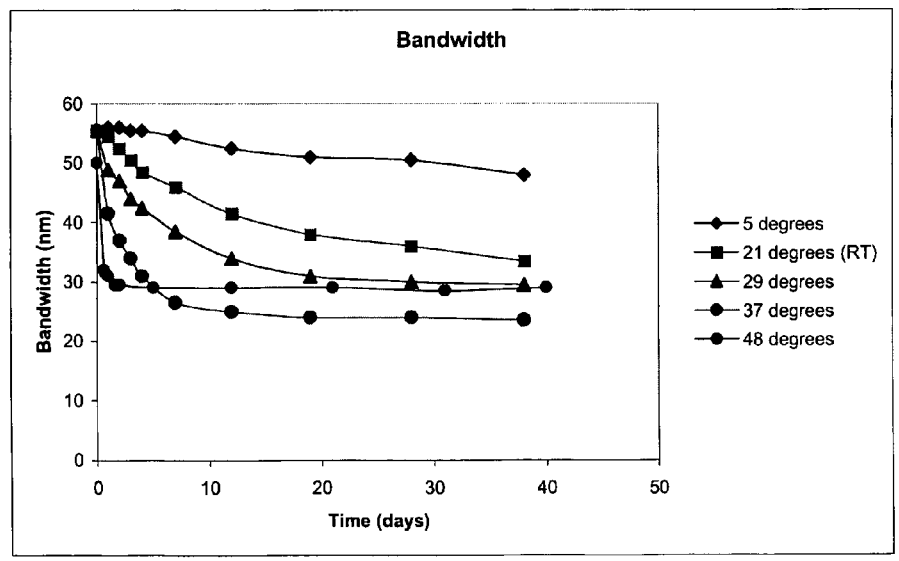
FIG. 12 shows graphs of UV bandwidth against time at different maturing temperatures of a batch of colloid produced according to the method of the invention of reducing silver nitrate with hydroxylamine phosphate.

Referring to FIG. 12, these graphs illustrate the effect of temperature on the maturing time of a colloid produced according to the method of invention of reducing silver nitrate with hydroxylamine phosphate. The results in this example are from monitoring the changes in the UV bandwidth of colloid solution (60 μl diluted in 3 ml water) in a 1 cm pathlength cuvette and show how the maturing period reduces as the temperature increases.

The data presented here are the results of carrying out an extended range of stability studies in polystyrene and glass containers and at a range of temperatures.

Hydroxylamine phosphate colloids (HPAg colloids), when produced in polystyrene containers initially, display UV spectra with a $\lambda_{max}$ value of typically 395 nm, a bandwidth of 57 nm and an absorbance of 0.280. Any batch of colloid produced will then over a period of typically 8 weeks (maturing period) show a decrease in the $\lambda_{max}$ to 389±1 nm, with a corresponding decrease in the bandwidth to 28±2 nm and increase in absorbance to 0.475±25. Thereafter these values have been found to remain constant for over 20 weeks, as may be seen in FIG. 10. Batches of colloid prepared in glass containers show the same initial UV characteristics but within 4 weeks lose stability and the silver aggregates and falls out of solution. Hence polystyrene is the preferred material for preparation and storage of the colloid Raman spectroscopy of maturing samples shows the SER (R)S intensity gradually increases and then after the maturing period of 8 weeks remain constant (FIG. 11). TEM studies indicate no change in either the particle size or distribution of the silver colloidal particles. From, these UV, Raman and TEM results it is postulated that when the colloid is first prepared, silver particles of the same size are formed but are held together in very small clumps, possibly by weak hydrogen bonding forces. On maturing possibly by interaction with the surface of the container, the small clumps dissociate into individual colloidal silver particles.

The changes observed in the UV properties of the colloid strongly support the postulation and if there is only a weak bonding force between the particles then it was reasoned that heating of the colloid solution should aid dissociation of the clumps of particles. This was confirmed by monitoring the UV properties of colloid samples stored in polystyrene containers over a range of temperatures between 4 and 55° C. Maturing periods of the colloidal solutions were reduced dramatically when samples were held at temperatures above room temperature with the maturing period decreasing as the temperature increased as may be seen from FIG. 12.

The UV properties of these matured colloids matched those obtained for a room temperature matured colloids. Similarly, Raman monitoring of the colloids during these maturing periods showed an increase in SER(R)S intensity but once matured the intensity remained constant and matched that of a room temperature matured colloid. No changes in the UV properties were detected for samples stored at 4° C.

The invention claimed is:

1. A method of producing a metal colloid solution, comprising adding an aqueous solution of a hydroxylamine salt to an aqueous solution of an alkali, and then introducing into the mixture an aqueous solution of the metal ions, the hydroxylamine salt being selected such that the anion, when combined with the said metal ions, would form a metal salt having a solubility product ($K_{sp}$) value of less than $1 \times 10^{-10}$ in water, wherein the metal ion solution is introduced into the mixture in such a manner that the metal ions are substantially dispersed throughout the mixture within one second.

2. A method according to claim 1, wherein the metal ions are introduces into and mixed with the mixture within 0.5 second.

3. A method according to claim 1, wherein the metal is silver.

4. A method according to claim 3, wherein the aqueous solution of metal ions is a solution of silver nitrate.

5. A method according to claim 1, wherein the metal is gold.

6. A method according to claim 5, wherein the aqueous solution of metal ions is a solution of hydrogen tetrachloroaurate.

7. A method according to claim 1, wherein the metal ion solution is introduced into the mixture as a high velocity stream.

8. A method according to claim 7, wherein the volume of the mixture into which the metal ion solution is introduced is less than 5 cm³.

9. A method according to claim 1, wherein after introduction of the metal ion solution the mixture is subjected to further mixing for a period of between 2 seconds and 30 seconds.

10. A method according to claim 1, wherein the alkali is sodium hydroxide.

11. A method according to claim 10, wherein the hydroxylamine salt is hydroxylamine phosphate.

12. A method according to claim 1, wherein the concentration of the hydroxylamine salt is $0.075 \times 10^{-3}$ M.

13. A method according to claim 1, wherein the concentration of the alkali is $1.33 \times 10^{-3}$ M.

14. A method according to claim 1, wherein the resultant particle size in the colloid is 19±9 nm.

15. A method according to claim 1, comprising carrying out the introduction and dispersion in a container made of polystyrene.

16. A method according to claim 15, wherein the colloid solution is stored before use in a container made of polystyrene.

17. A method according to claim 1, comprising maturing the colloid solution at a temperature above room temperature to 55° C. for a period of 1-12 days to improve stability.

18. A method according to claim 1, comprising maturing the colloid solution at a temperature in the range of 40° to 50° C.

19. A method according to claim 1, comprising maturing the colloid for 24 hours.

20. A metal colloid solution, formed by adding an aqueous solution of a hydroxylamine salt to an aqueous solution of an alkali, and then introducing into the mixture an aqueous solution of the metal ions, the hydroxylamine salt being selected such that the anion, when combined with the said metal ions, forms a metal salt having a solubility product ($K_{sp}$) value of less than $1 \times 10^{-10}$ in water.

21. A method of Raman spectroscopy using as a medium a metal colloid solution formed by adding an aqueous solution of a hydroxylamine salt to an aqueous solution of an alkali, and then introducing into the mixture an aqueous solution of the metal ions, the hydroxylamine salt being selected such that the anion, when combined with the said metal ions, forms a metal salt having a solubility product ($K_{sp}$) value of less than $1 \times 10^{-10}$ in water.

22. A method of producing a metal colloid solution, comprising adding and aqueous solution of hydroxylamine phosphate to an aqueous solution of an alkali, and then introducing into the mixture am aqueous solution of the metal ions, wherein the metal ion solution is introduced into the mixture and mixed therewith within one second.

* * * * *